(12) United States Patent  
Nygaard et al.

(10) Patent No.: US 9,539,025 B2  
(45) Date of Patent: *Jan. 10, 2017

(54) BIOPSY SYSTEM

(75) Inventors: Per Ehrenreich Nygaard, Søborg (DK); Gert Karlsson, Copennagen (DK); Tommy Bjørn Olsen, Vangedevej (DK); Bjørn Fortling, Vestergade (DK); Lis Sørensen, legal representative, Kokkedal (DK)

(73) Assignee: B-K Medical Aps, Herlev (DK)

( * ) Notice: Subject to any disclaimer, the term of this patent is extended or adjusted under 35 U.S.C. 154(b) by 1443 days.

This patent is subject to a terminal disclaimer.

(21) Appl. No.: 12/225,469

(22) PCT Filed: Mar. 23, 2007

(86) PCT No.: PCT/DK2007/000142  
§ 371 (c)(1),  
(2), (4) Date: Feb. 27, 2009

(87) PCT Pub. No.: WO2007/110076  
PCT Pub. Date: Oct. 4, 2007

(65) Prior Publication Data  
US 2009/0171218 A1    Jul. 2, 2009

Related U.S. Application Data

(60) Provisional application No. 60/785,374, filed on Mar. 24, 2006.

(51) Int. Cl.  
*A61B 10/02*    (2006.01)  
*A61B 8/12*    (2006.01)  
(Continued)

(52) U.S. Cl.  
CPC ......... *A61B 17/3403* (2013.01); *A61B 8/0833* (2013.01); *A61B 8/0841* (2013.01);  
(Continued)

(58) Field of Classification Search  
CPC ....................................................... A61B 8/12  
See application file for complete search history.

(56) References Cited

U.S. PATENT DOCUMENTS 4,346,717 A * 8/1982 Haerten ......................... 600/461  
4,402,324 A * 9/1983 Lindgren et al. ............. 600/461  
(Continued)

FOREIGN PATENT DOCUMENTS

EP    0 955 010 A1    11/1999  
JP    2-71732    3/1990  
(Continued)

OTHER PUBLICATIONS

International Search Report for International Application No. PCT/DK2007/000142, dated Feb. 8, 2007 (2 pages).  
(Continued)

*Primary Examiner* — Katherine Fernandez  
*Assistant Examiner* — Farshad Negarestan  
(74) *Attorney, Agent, or Firm* — Anthony M. Del Zoppo, III; Driggs, Hogg, Daugherty & Del Zoppo, Co., LPA

(57) ABSTRACT

A biopsy assembly for collecting tissue samples by means of a biopsy needle when introduced in a body cavity. The biopsy assembly comprises an elongated member (101), with a longitudinal axis (102), configured with: a first needle guide (203) arranged to guide a needle in a direction transverse to the longitudinal axis (102), and a second needle guide (204, 303) arranged to guide a needle in a direction along the elongated member (101).

15 Claims, 9 Drawing Sheets

(51) Int. Cl.
*A61B 17/34* (2006.01)
*A61B 8/08* (2006.01)

(52) U.S. Cl.
CPC ............ *A61B 8/12* (2013.01); *A61B 10/0233* (2013.01); *A61B 2017/3413* (2013.01); *A61B 2017/3447* (2013.01)

(56) References Cited

U.S. PATENT DOCUMENTS

| | | | | |
|---|---|---|---|---|
| 4,469,106 A | * | 9/1984 | Harui | A61B 8/0833 600/461 |
| 4,475,553 A | * | 10/1984 | Yamaguchi et al. | 600/461 |
| 4,497,325 A | * | 2/1985 | Wedel | 600/567 |
| 4,542,747 A | * | 9/1985 | Zurinski et al. | 600/461 |
| 4,567,896 A | * | 2/1986 | Barnea et al. | 600/443 |
| 4,681,103 A | * | 7/1987 | Boner et al. | 606/1 |
| 4,733,661 A | * | 3/1988 | Palestrant | 606/108 |
| 4,883,053 A | * | 11/1989 | Simon | 606/130 |
| 4,899,756 A | * | 2/1990 | Sonek | 600/461 |
| 4,911,173 A | * | 3/1990 | Terwilliger | 600/464 |
| 5,235,987 A | * | 8/1993 | Wolfe | A61B 8/0833 600/461 |
| 5,623,931 A | * | 4/1997 | Wung et al. | 600/461 |
| 5,647,373 A | * | 7/1997 | Paltieli | 600/567 |
| 5,681,276 A | | 10/1997 | Lundquist | |
| 5,681,277 A | | 10/1997 | Edwards et al. | |
| 5,687,729 A | * | 11/1997 | Schaetzle | 600/439 |
| 5,758,650 A | * | 6/1998 | Miller et al. | 600/461 |
| 5,817,022 A | * | 10/1998 | Vesely | 600/443 |
| 5,941,889 A | * | 8/1999 | Cermak | 606/130 |
| 5,943,719 A | * | 8/1999 | Feldman et al. | 606/130 |
| 5,957,850 A | | 9/1999 | Marian, Jr. et al. | |
| 5,984,930 A | * | 11/1999 | Maciunas et al. | 606/130 |
| 6,045,508 A | | 4/2000 | Hossack et al. | |
| 6,055,449 A | * | 4/2000 | Navab | 600/427 |
| 6,059,731 A | | 5/2000 | Seward et al. | |
| 6,083,176 A | * | 7/2000 | Terwilliger | 600/562 |
| 6,203,499 B1 | * | 3/2001 | Imling et al. | 600/461 |
| 6,228,039 B1 | * | 5/2001 | Binmoeller | 600/566 |
| 6,261,234 B1 | * | 7/2001 | Lin | 600/461 |
| 6,283,925 B1 | * | 9/2001 | Terwilliger | 600/568 |
| 6,296,614 B1 | * | 10/2001 | Pruter | 600/461 |
| 6,361,499 B1 | * | 3/2002 | Bates et al. | 600/461 |
| 6,379,307 B1 | * | 4/2002 | Filly et al. | 600/461 |
| 6,405,733 B1 | * | 6/2002 | Fogarty et al. | 128/899 |
| 6,433,902 B1 | | 8/2002 | Chiaroni et al. | |
| 6,443,902 B1 | * | 9/2002 | Sasady | 600/461 |
| 6,447,477 B2 | * | 9/2002 | Burney et al. | 604/93.01 |
| 6,475,152 B1 | * | 11/2002 | Kelly et al. | 600/461 |
| 6,485,426 B2 | * | 11/2002 | Sandhu | 600/461 |
| 6,490,467 B1 | * | 12/2002 | Bucholz et al. | 600/407 |
| 6,512,943 B1 | * | 1/2003 | Kelcz | 600/436 |
| 6,524,247 B2 | * | 2/2003 | Zhao et al. | 600/437 |
| 6,591,129 B1 | * | 7/2003 | Ben-Haim et al. | 600/424 |
| 6,626,832 B1 | * | 9/2003 | Paltieli et al. | 600/439 |
| 6,671,538 B1 | * | 12/2003 | Ehnholm et al. | 600/425 |
| 6,695,786 B2 | * | 2/2004 | Wang et al. | 600/461 |
| 6,702,749 B2 | * | 3/2004 | Paladini et al. | 600/464 |
| 6,731,966 B1 | * | 5/2004 | Spigelman et al. | 600/407 |
| 6,733,458 B1 | * | 5/2004 | Steins et al. | 600/461 |
| 6,884,219 B1 | * | 4/2005 | Pruter | 600/459 |
| 7,008,383 B1 | * | 3/2006 | Damadian et al. | 600/567 |
| 2001/0001811 A1 | * | 5/2001 | Burney et al. | 604/93.01 |
| 2002/0035864 A1 | * | 3/2002 | Paltieli et al. | 73/1.01 |
| 2002/0123689 A1 | * | 9/2002 | Furia | A61B 8/0833 600/461 |
| 2002/0133079 A1 | * | 9/2002 | Sandhu | 600/464 |
| 2002/0156376 A1 | * | 10/2002 | Wang et al. | 600/439 |
| 2003/0028112 A1 | * | 2/2003 | Paladini et al. | 600/439 |
| 2003/0078502 A1 | * | 4/2003 | Miyaki et al. | 600/461 |
| 2003/0105410 A1 | * | 6/2003 | Pearlman | 600/547 |
| 2003/0109825 A1 | * | 6/2003 | Loser | 604/131 |
| 2003/0130575 A1 | * | 7/2003 | Desai | A61B 8/0841 600/417 |
| 2003/0135119 A1 | * | 7/2003 | Lee et al. | 600/461 |
| 2003/0199753 A1 | * | 10/2003 | Hibner et al. | 600/411 |
| 2003/0212414 A1 | * | 11/2003 | Sonek | 606/130 |
| 2003/0233046 A1 | * | 12/2003 | Ferguson et al. | 600/437 |
| 2004/0068191 A1 | | 4/2004 | Seward et al. | |
| 2004/0077972 A1 | * | 4/2004 | Tsonton et al. | 600/564 |
| 2004/0133122 A1 | * | 7/2004 | Pearlman | 600/547 |
| 2004/0267121 A1 | * | 12/2004 | Sarvazyan et al. | 600/439 |
| 2005/0020938 A1 | * | 1/2005 | Nygaard et al. | 600/564 |
| 2005/0143753 A1 | * | 6/2005 | Whitmore et al. | 606/130 |
| 2005/0203413 A1 | * | 9/2005 | Fichtinger et al. | 600/461 |
| 2005/0267373 A1 | * | 12/2005 | Lee | 600/471 |
| 2006/0036176 A1 | | 2/2006 | Angelsen et al. | |
| 2006/0064010 A1 | * | 3/2006 | Cannon et al. | 600/434 |

FOREIGN PATENT DOCUMENTS

| | | |
|---|---|---|
| WO | WO 94/13208 | 6/1994 |
| WO | WO-96/10958 | 4/1996 |
| WO | WO 98/38486 | 9/1998 |
| WO | WO-99/34735 | 7/1999 |
| WO | WO-00/19906 | 4/2000 |

OTHER PUBLICATIONS

International Search Report for International Application No. PCT/DK2007/000144, dated May 12, 2007 (3 pages).

* cited by examiner

BIOPSY SYSTEM

CROSS-REFERENCE TO RELATED APPLICATIONS

This application is a national phase application of International Application No. PCT/DK2007/000142, filed Mar. 23, 2007, and claims the benefit of U.S. Provisional Application No. 60/785,374, filed Mar. 24, 2006, the content of both of which is incorporated herein by reference.

BACKGROUND

Various ultrasound techniques and devices have been developed for imaging the interior of a body e.g. the human body. One application of ultrasound imaging has been in the medical field, and in particular, in endocavitary probes (e.g., biopsy guidance endocavitary probes). Such probes may be used, for example, for endovaginal examination (e.g., to examine the uterus, ovaries, etc.), endorectal examination (e.g., to examine the rectal wall, prostate, etc.), and/or other medically-related applications. It should be noted that for instance endorectal examination is rather unpleasant and that biopsy taking is rather painful and therefore typically requires local anaesthesia.

Endocavitary probes typically have an elongated rod-like shape configured with a handle that extends as a portion of the elongated rod-like shape, but in the end opposite the distal end. Other ultrasound probes are, contrary to endocavitary probes, configured for placing the probe on the skin of the body to provide imaging of the interior of the body located beneath the skin. Still other probes (e.g. intraoperative probes) are configured for placing the probe directly on organs inside the body during surgery operations.

RELATED PRIOR ART

JP 02071732-A discloses an elongated ultrasound probe for biplane ultrasound imaging of a prostate. The elongated probe comprises an end portion with a longitudinally arranged transducer array for sagittal imaging and a transversely arranged transducer array for transverse imaging, where the longitudinally arranged array is placed perpendicular to the transversely arranged array, but on the more distal end of the end portion, such that the image planes of the two transducers intersect orthogonally. The arrays are formed in a convex arc shape so as to provide the image planes from radial scan lines. The arc shapes have a relatively smooth shape.

The ultrasound probe is disclosed interconnected with a biopsy needle guide configured for guiding a biopsy needle longitudinally to the elongated ultrasound probe, but offset a certain distance from the probe. The biopsy needle guide is configured such that the biopsy needle is guided through the opening of the body cavity and penetrates the body from the interior of the body cavity.

U.S. Pat. No. 6,443,902-B1 discloses an ultrasound probe with a detachable needle guide for collecting tissue samples. The ultrasound probe is configured for insertion into a body cavity and comprises two transducer arrays and a needle guide assembly for guiding a biopsy needle. The transducer arrays are arranged perpendicular to each other like described above, so as to provide bi-plane imaging.

The needle guide assembly is separate from, but can be interconnected with the ultrasound probe. The ultrasound probe can be covered by a soft sheath and the needle guide assembly can then be attached to the probe, but such that the sheath prevents contact between the probe and assembly. Thus, the needle guide is arranged outside the sheath in such a manner that a needle of the needle guide need not penetrate the sheath. Thereby, only the assembly, but not the probe needs sterilization after use. The needle guide is arranged to guide the needle in a direction transverse to a longitudinal axis of the elongated ultrasound probe. The biopsy needle guide is configured such that the biopsy needle is guided through the opening of the body cavity and penetrates the body from the interior of the body cavity.

U.S. Pat. No. 6,261,234-B1 discloses a probe for providing simultaneous viewing of an instrument in two ultrasound imaging planes (biplane instrument guidance).

The probe is configured as an elongated member with an end-portion that is configured to accommodate two transducer arrays. The two transducer arrays are in the form of a side-fire transducer array and end-fire transducer array arranged along a respective convex arc shape to provide two imaging planes. The two imaging planes intersect at a line which coincides with an instrument path. A needle guide in the form of a groove of the probe is arranged to guide the needle along the instrument path when it protracts from the groove. Seen towards the end-portion, the transducer arrays are arranged in an L-shaped configuration, where the groove has an opening, wherefrom the needle protracts, at the corner of the L-shape.

Despite the above prior art documents disclosing important improvements, the cited prior art documents do not fully take advantage of the possibilities related to patient comfort and effectiveness/efficiency in medical diagnosis situations.

A known configuration comprises a biopsy needle guide for guiding a needle a long a path longitudinal to, but offset from a rod-shaped probe and a side-fire monitoring of the path (cf. U.S. Pat. No. 6,443,902-B1, FIG. 1). However, this configuration poses problems when used for taking biopsies of a prostate. A biopsy regimen can include e.g. at least two biopsies from the apical area of the prostate (closest to the pelvic floor muscles). In this situation the biopsy needle will first penetrate into the human tissue at a small, but sometimes significant distance behind the sagittal image projection which projects from the first transducer. Examining the anatomy slightly below the apex more closely identifies the different pelvic floor muscles. It is then clear that any attempt to introduce a biopsy needle along, but offset from the probe will cause the needle to come close to—or even pass through parts of the muscles which is painful.

SUMMARY OF THE INVENTION

Therefore, expediently, a needle guide is arranged to guide a needle in a direction transverse to the longitudinal axis, and a second needle guide is arranged to guide the needle in a direction along the elongated member.

The transversely guided biopsy needle is thus guided through the opening of the body cavity and penetrates the body from the interior of the body cavity. Thereby, the basal area of the prostate can be sampled by biopsy while being safely monitored by the side-fire imaging. The longitudinally guided biopsy needle is also guided through the opening of the body cavity (very close to the periphery of the probe) and penetrates the body from the interior of the body cavity. Likewise, but when rotated about 90 degrees and introduced into the body at a steeper angle, the apical area of the prostate can be sampled by biopsy. Thereby, the prostate apex and basal can be sampled by biopsy in the same cycle.

The combination of the transversely guided biopsy needle and longitudinally guided biopsy needle provides a superior probe for taking biopsies of a prostate in a single cycle of operations.

Preferably, the first needle guide is arranged to provide an angle between the needle, when inserted into the needle guide, and the longitudinal axis of the elongated member within the range of 10 to 50 degrees. The needle guide can be shaped as a substantially straight tube or curved tube.

Preferably, the first needle guide provides an angle of a needle, when inserted into the first needle guide, at its projection from the first needle guide and the longitudinal axis of the elongated member within the range of 10 to 50 degrees. The projection of the needle can be controlled by the needle guide to obtain the desired angle of protraction.

Expediently, the needle guides are arranged, with respect to the elongated member, to make the needles, when inserted into the needle guides, protract at opposite positions with respect to a cross-section of the biopsy assembly. Thereby, the relevant locations for taking samples of the tissue under examination can be addressed by the paths of the biopsy needles by firstly using the first needle guide to take first biopsies (removing the biopsy needle) and then simply rotating the probe to take second biopsies. This is far more convenient than actually changing probe.

In a preferred embodiment, the second needle guide extends along the periphery of the elongated member, but offset from the periphery in a direction away from the point of gravity in a cross-sectional view of the elongated member.

In a preferred embodiment, the elongated member has a shape that is configured for mechanical interconnection with a probe and to match a recess of a probe so as to provide a combination of the assembly and probe, when interconnected, that can be circumscribed by a cylinder that covers at least a portion of the length of the elongated member and has a diameter that is within the range of 12 to 30 millimeters.

The elongated member is configured with coupling means for interconnection with an ultrasound probe with complementary coupling means.

The needle guides may be shaped as a tube with an entry end configured for entry of a needle and an exit end configured for the needle to project from the needle guide. The smooth shape of a tube has a smaller tendency to collect dirt and remainders of tissue, since there are fewer protrusions.

To reduce the risk of confusing the acquired images, marking on biopsy needle guides may correspond to marking of acquired bi-plane images, respectively, when displayed on a display screen.

There is also provided an ultrasound probe for cavity scanning of a body and for guiding a biopsy needle. The ultrasound transducer is configured with: an ultrasound transducer to provide an imaging plane; a first needle guide configured to guide an elongated needle and arranged to guide the needle in a direction transverse to the longitudinal axis, and a second needle guide configured to guide an elongated needle and arranged to guide the needle in a direction longitudinal to the elongated member.

BRIEF DESCRIPTION OF THE DRAWINGS

Preferred embodiments will be described in greater detail and with reference to the drawing in which.

DESCRIPTION OF A PREFERRED EMBODIMENT

Figure 1:
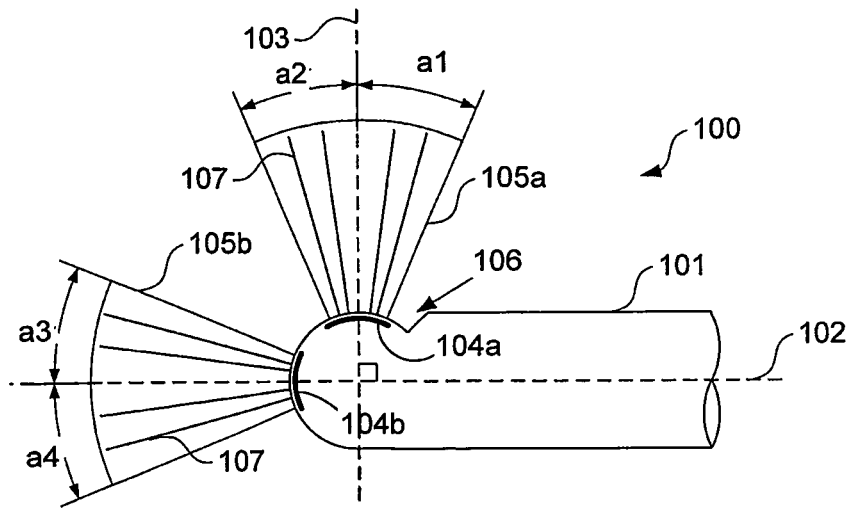
FIG. 1 shows a cross-sectional view of an ultrasound probe comprising a transducer array with a field of view.

FIG. 1 shows a cross-sectional view of an ultrasound probe comprising a transducer array with a field of view. The ultrasound probe 100 is configured for cavity scanning of a body in that it has an elongated or rod-like shape which can be introduced into the cavity. In general such an ultrasound probe has a handle, a shaft and a distal end configured to accommodate an ultrasound transducer 104a; 104b. Only the portion of the shaft towards the distal end is shown—the handle is not shown. The distal end of the probe may also be denoted a scanning head or the scanning end of the probe. The probe or rather the distal end of it may also be seen as a housing in that it accommodates transducer array. In general the probe has the shape of an elongated member.

A longitudinal axis 102 of the probe or elongated member is shown as a dashed line. A transverse axis 103 perpendicular to the longitudinal axis 102 is also shown as a dashed line.

In one aspect, the probe 100 is configured to accommodate at its distal end a first transducer in the form of two detached arrays 104a;104b of ultrasound transducer elements. The two arrays 104a;104b are arranged in extension of one another, but at an offset distance in the direction of extension. However, the offset distance may be so small that the arrays provide imaging corresponding to a single array. In another aspect, as described further below, the first transducer is in the form of a single array. The arrays or array provide(s) an imaging plane coinciding with the longitudinal axis 102 and transverse axis 103 i.e. the axes lies in the imaging plane. For medical uses, this imaging plane is also denoted a sagittal imaging plane.

The transducer arrays 104a,104b are shaped so as to provide a desired field of view in the sagittal imaging plane. It is in general desired to use small (i.e. short) arrays. Consequently, the arrays are shaped along a convex arc shape to emit and receive ultrasound wave energy along radial scan lines. The radial structure of the scan lines provides a sector of a circle which becomes broader with the distance to the transducer. The smaller the radius of the convex arc shape, the broader the sector of the circle. The above is based on a circular arc shape. However, other arc shapes that provide radial scan lines can be used. Such other arc shapes can comprise sections of straight linear arrays each comprising a number of transducer elements. Complex arc shapes comprising sections with. different radiuses can also be applied to obtain a desired field of view.

Since in general small clearance or close contact between the transducer and the housing of the distal end is desired, the shape of the transducer dictates the shape of the housing about the transducer. In the shown configuration, the housing and the transducer have the shape of a portion of a circular arc. Since it is an objective to provide a design of the probe which is suitable for cavity scanning and thus for suitable for being introduced into the cavity, the probe has a depression 106 behind the housing that accommodates the transducer arrays 104a,104b. Thereby the field of view 105a about the transverse axis 103 is allowed to extend further towards the handle end of the probe without requiring a larger diameter of the housing.

The arrays 104a and 104b of the first transducer provide partial fields of view 105a and 105b, respectively. The field of view 105a,105b provided by the first transducer 104a, 104b covers more than 15 degrees of scan lines at each side of its intersection with the longitudinal axis 102 and more than 15 degrees of scan lines at each side of its intersection with a transverse axis 103. Thus angles a1, a2, a3 and a4 are larger than 15 degrees. The angles need not be equal. In a preferred embodiments a1 plus a2 is approximately equal to a3 plus a4.

For most practical purposes a partial field of view of more than 30 degrees is desired. Thus, preferably, the field of view, at each side of its intersection with the longitudinal axis or transverse axis, covers a radial section larger than an angle selected from the group of 20, 25, 30, 35, 40, 45, 50 and 55 degrees.

It is shown that the first transducer has partial fields of view which are centred about the longitudinal axis 102 and the transverse axis 103. It is also shown that the field of view 105b established about the longitudinal axis 102 and the field of view 105b established about the transverse axis 103 are of substantially same size.

Figure 2:
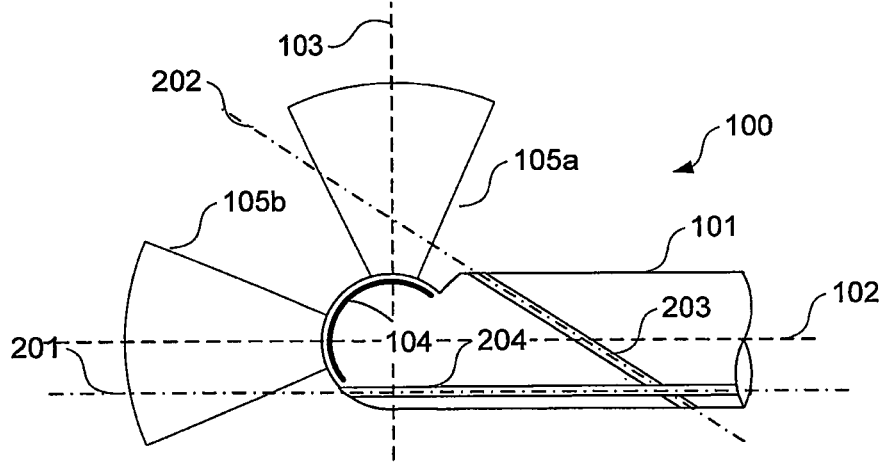
FIG. 2 shows a cross-sectional view of an ultrasound probe comprising a needle guide arranged longitudinally and a needle guide arranged transversely.

FIG. 2 shows a cross-sectional view of an ultrasound probe comprising a needle guide arranged longitudinally and a needle guide arranged transversely. This arrangement of the needle guides enhances the use of the ultrasound probe to be used for taking biopsy samples along two different biopsy paths while providing safe monitoring of both the paths.

The transverse needle guide 203 and longitudinal needle guide 204 can, as shown, be integrated with the probe body 101. Alternatively, as described further below, the probe can be configured with coupling means for interconnection with a biopsy assembly with complementary coupling means.

The probe body 101 comprises a first, transverse needle guide 203 configured to guide a needle along a path 202 which intersects with the field of view 105a established about the transverse axis 103. It further comprises a second, longitudinal needle guide 204 configured to guide a needle along a path 201 which intersects with the field of view 105b established about the longitudinal axis 102. Thereby, a needle or other instrument guided, by means of the needle guide, along one of the paths will intersect with at least some of the scan lines of the respective fields of view and thus be viewable during the ultrasound scanning. Thereby safe monitoring of both the paths is provided.

The transverse needle guide 203 guides a needle along the path 202. This path intersects the scan lines of the field of view 105a established about the transverse axis 103 at angles say between about 25 to 90 degrees. Thereby, the path 202 is viewable across the entire field of view.

The transverse needle guide is arranged to provide an angle between the needle, when inserted into the needle guide, and the longitudinal axis of the elongated member within the range of 10 to 50 degrees, preferably at about 15 to 20 degrees e.g. at 17 degrees.

For a straight transverse needle guide, the same angle is provided along the entire path 202. But a needle guide configured to provide a curved path can also be employed. Such a curved guide can provide an angle of a needle, when inserted into the first needle guide, at its projection from the first needle guide and the longitudinal axis of the elongated member within the range of 10 to 50 degrees. Generally, the curved path is configured with a curvature larger than 20 millimeters and/or 25 millimeters and/or 30 millimeters and/or 35 millimeters and/or 40 millimeters. Thereby it is possible to guide a biopsy needle, which is configured with sufficient strength and volume to take out a biological sample and hence has only a limited flexibility.

The longitudinal needle guide 204 guides a needle along the path 201. This path intersects the scan lines of the field of view 105b established about the longitudinal axis 102 at angles say between about 5 to 25 degrees. Thereby, the path 201 is viewable only at a partial sector of the field of view.

Seen along the longitudinal axis 102 at a point more distal than the housing of the probe and towards the housing of the probe, the needle guides are arranged, with respect to the elongated member, to make the needles, when inserted into the needle guides, protract at opposite positions with respect to a cross-section of the biopsy assembly. Thus, e.g. a prostate can be addressed by either one of the paths 201,202 by rotating the probe 180 degrees about its longitudinal axis.

In this embodiment, the first transducer is configured as a single array 104. Thereby, the signals to and from the elements of the transducer array can be elected electronically so as to provide differently sized or positioned images from the transducer array. This will be explained in greater detail further below.

Figure 3:
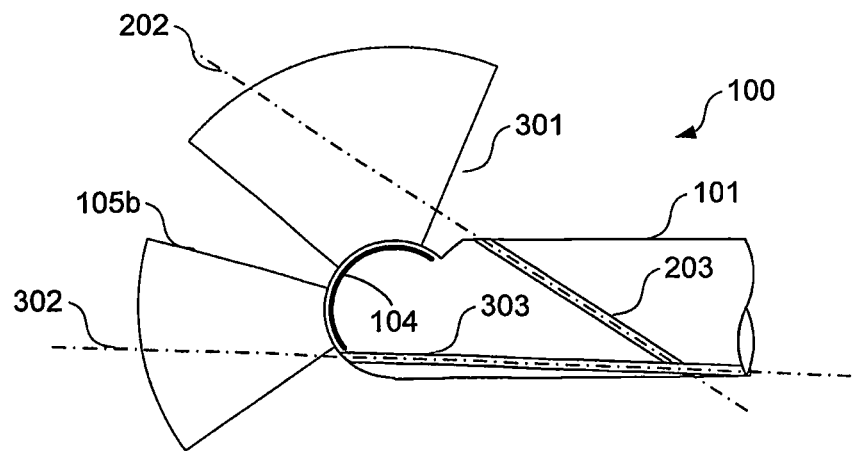
FIG. 3 shows a cross-sectional view of an ultrasound probe comprising a needle guide arranged along the ultrasound transducer, but inclined.

FIG. 3 shows a cross-sectional view of an ultrasound probe comprising a needle guide arranged along the ultrasound transducer, but inclined. In this embodiment, one of the needle guides 303 extends in a direction along the elongated member 101. This direction may be parallel to a longitudinal axis of the elongated probe or, as shown, inclined with respect to a longitudinal axis of the elongated probe. This inclination is preferably arranged such that the path 302 crosses the longitudinal axis in front of the transducer 104. The needle guide 303 can be configured as a straight channel or a curved channel. Thus, the inclination need not be present—or be the same—along the entire length of the guide 303.

Figure 4:
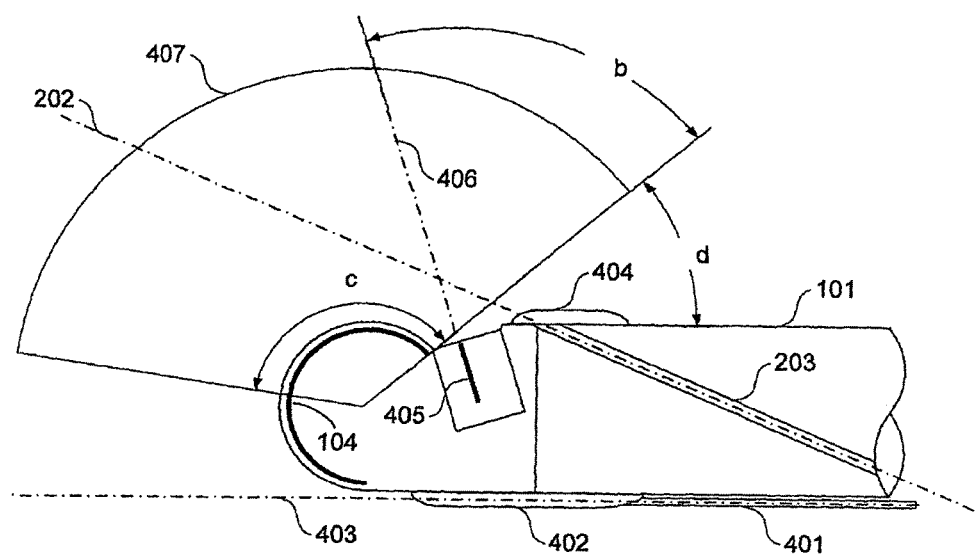
FIG. 4 shows a cross-sectional view of an ultrasound probe in a mode providing sagittal side-fire imaging and a transverse imaging.

FIG. 4 shows a cross-sectional view of an ultrasound probe in a mode providing bi-plane imaging. The bi-plane imaging is provided by sagittal side-fire imaging and transverse imaging. The transverse imaging is provided by a second transducer array 405 to provide a second image plane 406 transverse to the longitudinal axis of the elongated member. Preferably, the second image plane 406 is orthogonal to the first image plane 407. The second image plane is also denoted the transverse image plane.

The transverse image plane 406 may be arranged so as to coincide with the axis 103 transverse (perpendicular) to the longitudinal axis 102 i.e. at right angles or about right angles. However, as shown, it is preferred that the second transducer array is inclined to provide the transverse image plane at an angle of less than 90 degrees with respect to the longitudinal axis towards the distal end of the elongated member. The transverse image plane 406. is shown at an angle of about (180 degrees minus 107 degrees equal to) 73 degrees relative to the longitudinal axis 102. Preferably, the second transducer is inclined to provide the second image plane at an angle that is within the range of 40 to 85 degrees with respect to the longitudinal axis towards the one end of the elongated member.

As the second transducer 405 is arranged in an inclined position close to the first transducer 104, the image plane 406 provided by the second transducer intersects the field of view provided by the first transducer. Thereby, since some spatial locations appear in both imaging planes, the ability provided by the second imaging plane 406 to scan outside the sagittal imaging plane 407 can improve spatial location determination. As it can be seen, the transverse field of view will intersect only scan lines of a sector the first field of view i.e. a partial sector of the first field of view.

As it is shown, the first transducer 104 is arranged at the one end of the elongated member 101, but on the more distal portion of the end than the second transducer array 405.

It is also shown that only a portion (i.e. a 131.7 degrees sector closest to the transverse array 405) of the first transducer 104 is used for providing the sagittal field of view i.e. the portion enclosed by the depicted field of view 407. The remaining portion of the first transducer 104 may or may not be used when the probe is in a mode where bi-plane imaging is provided.

In this embodiment the transverse needle guide comprises a channel 203 which extends at its distal end into a projection 404. The longitudinal needle guide comprises a channel 401 which extends at its distal end into a projection 402. An instrument e.g. needle follows the path 403.

Preferably, the distal opening of the channel 203 is located relative to the (left side boundary of the) field of view 407. Thereby, the path 202 can be monitored/scanned when the needle starts to protract from the opening of the channel 203 and could potentially damage tissue or organs of a body.

The angle b designates the inclination of the transverse field of view 406 relative to the left boundary of the (sagittal) image plane (407). The angle c designates the coverage of the (sagittal) field of view 407. The angle d designates the angle between the longitudinal axis and the left boundary of the (sagittal) image plane (407).

Figure 5:
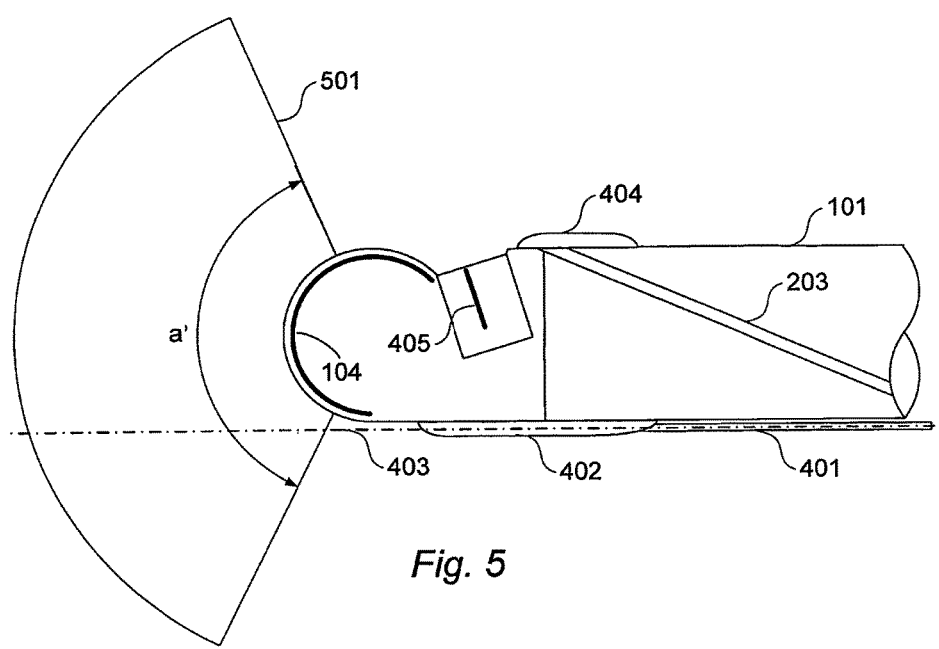
FIG. 5 shows a cross-sectional view of an ultrasound probe in a mode providing sagittal end-fire imaging.

FIG. 5 shows a cross-sectional view of an ultrasound probe in a mode providing sagittal end-fire imaging. In this mode another portion of the first transducer array is used for acquiring the image (image signals). The end-fire image is provided from a field of view corresponding to a sector of a circle of about 140 degrees. The field of view 501 is substantially centred about a longitudinal axis 102 of the probe 101. However, this centring may deviate about ±4 degrees as the elements of the array may be located such that perfect centring is inconvenient. The angle e designates the coverage of the sagittal end-fire view 501.

The probe can be operated in one of two modes: one mode providing side fire imaging or bi-plane imaging comprising side-fire imaging and another mode providing end-fire imaging. Preferably the probe is configured to enable selection of a first mode wherein an end-view image is acquired from a first portion of the first transducer array with a field of view that covers scan lines at each side of the longitudinal axis. It is possible to shift to a second mode wherein a side-view image is acquired from a second portion of the first transducer array with a field of view that covers scan lines at each side of the transverse axis. In the second mode the transverse image is also acquired. The modes can be selected either by operating one or more buttons on the probe or at the image-processor console.

Figure 6:
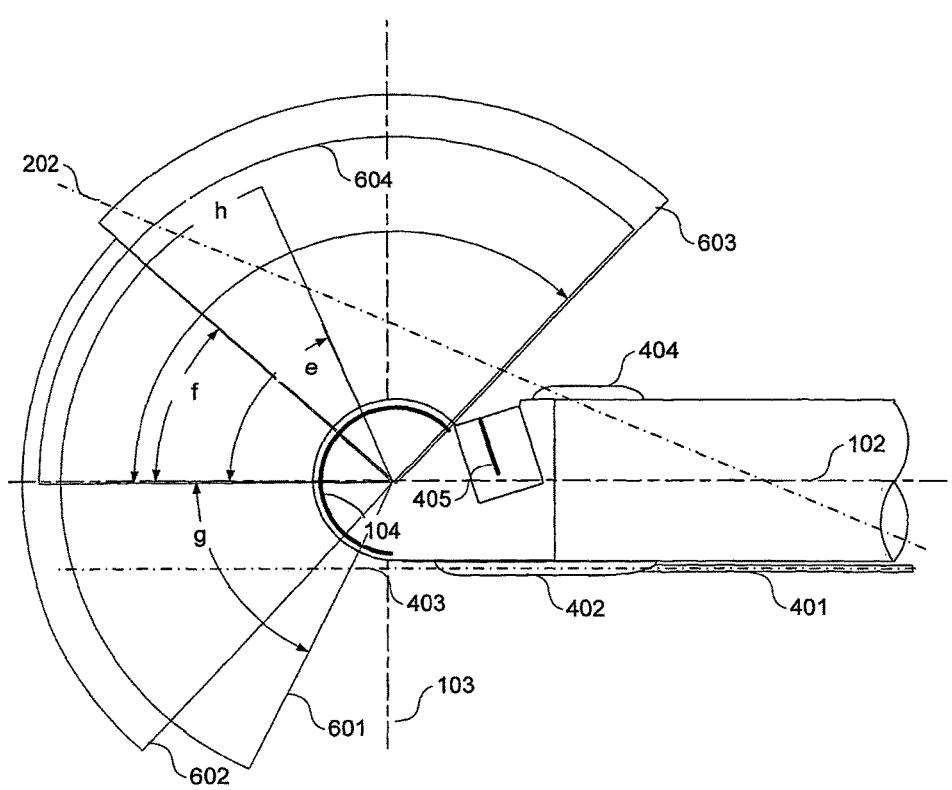
FIG. 6 shows a cross-sectional view of an ultrasound probe shown with different field of views.

FIG. 6 shows a cross-sectional view of an ultrasound transducer shown with different fields of views. Four different fields of views in the sagittal image plane obtainable by the first transducer is shown. Two end-fire fields of views and two side-fire fields of views are shown.

A first end-fire view 601 has a broader angular coverage than a second end-fire view 602. The first end-fire view 601 covers a circular section of about 132 degrees. The second end-fire view 602 covers a circular section of about 84 degrees.

A first side-fire view 604 has a broader angular coverage than a second side-fire view 603. The first side-fire view 604 covers a circular section of about 90 degrees. The second end-fire view 602 covers a circular section of about 132 degrees.

The second end-fire view 602 and the second side-fire view 603 are positioned next to each other and have in combination a non-overlapping coverage. If these side-fire and end-fire views are the desired views for all uses of the probe, the first array 104 need not cover a larger field of view. However, these side-fire and end-fire views may also represent electronically selected fields of views from the— larger—field of view provided by the first transducer.

The first end-fire view 601 and the first side-fire view 604 are positioned such that they establish a common field of view or overlap. This may be desired in any event since the common field of view improves the ability to keep a reference location when switching from the side-view to the end-view and vice versa. However, this may also be so since the field of view provided by the first transducer array has a limited length. Thus, the fields of view (or sectors) are arranged to cover a common sector of scan lines.

The angle f designates the angle between the longitudinal axis and the left side boundary of the (sagittal) field of view 603 and the angle g designates the angle between the longitudinal axis and the left side of view 601. Angle h designates the coverage of view 601.

The probe will typically comprise electronic circuitry configured with a multiplexer for a combined parallel and time-multiplexed output of image data.

Figure 7A:
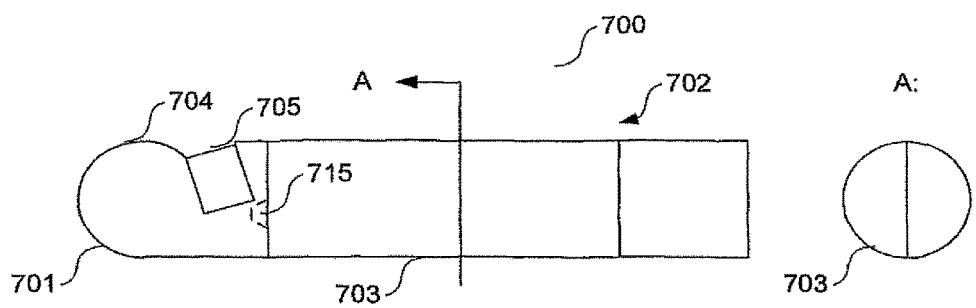
FIGS. 7a-b show a side-view and a top-view of an ultrasound probe with a recess for accommodating a biopsy assembly.
Figure 7B:
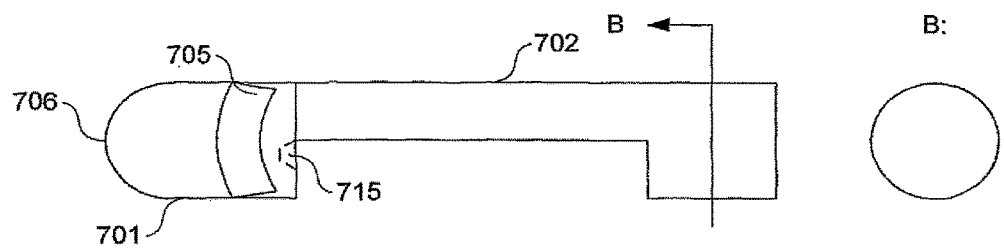

FIG. 7a-b shows a side-view and a top-view of an ultrasound probe with a recess for accommodating a biopsy assembly. In this embodiment, the biopsy assembly comprises the needle guides and is detachable from the ultrasound probe 700. The probe comprises an elongated shaft 702 with a recess 703 and a distal end with a housing 701 configured to accommodate the transducer arrays (not shown). The housing 701 (or scanner head) constitutes a portion of the probe 700. As shown the housing 701 has a cross-section which matches the cross-section of the shaft so as to form a probe with no sharp protrusions. The housing 701 has portions or windows 704,705 behind which the transducer arrays are mounted. The windows are optimized for transmission of ultrasound between the transducers and the medium to be scanned that surrounds the probe during use.

An indentation or notch 715 provides a fixation hole of the assembly.

Figure 7C:
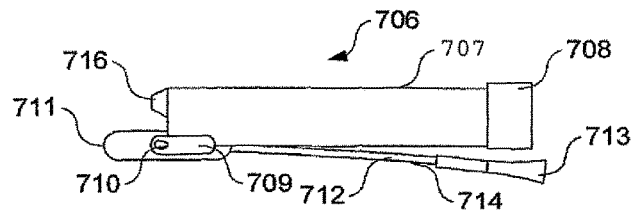
FIGS. 7c-d show a top-view and a side-view of a biopsy assembly.
Figure 7D:
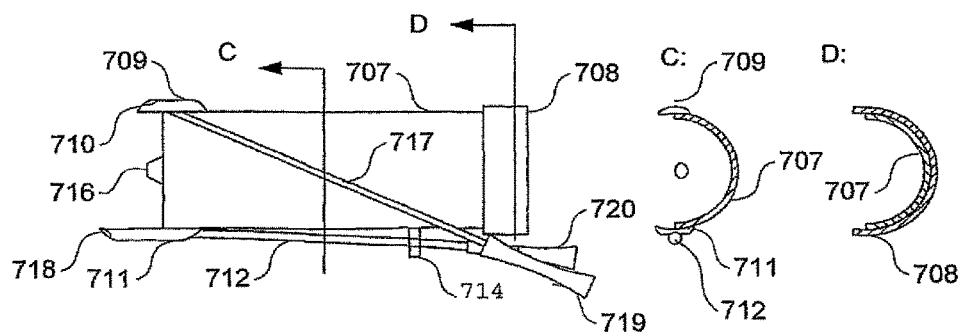

FIGS. 7c-d show a top-view and a side-view of a biopsy assembly. The biopsy assembly 706 comprises the needle guides and is detachable from the ultrasound probe 700.

The biopsy assembly 706 has an elongated member 707 with a cross-section in the shape of a half-section of a tube (e.g. a semi-cylindrical member). This cross-section of the elongated member matches the recess 703 of the probe so as for the assembly to be interconnected with the probe and form an interconnected probe and assembly which is relatively smooth and which is relatively closely interconnected such that larger slits or slots between the probe and assembly are avoided.

A collar 708 provides fixation of the assembly at the handle-end of the probe. At the opposite end of the elongated member a knob or pin 716, when engaging with the notch 715, provides locking of the assembly at the distal end of the probe. Retention is further improved by an upper lip 709 and a lower lip 711 which engage with a portion of the periphery of the probe.

The upper lip 709 and lower lip 711 are configured with openings 710 and 718 wherefrom instruments inserted into the channels 717 and 712 can protract to follow the biopsy paths into the tissue under examination.

The needle guide 712 extends along the periphery of the elongated member 707, but offset from the periphery in a direction away from the point of gravity in a cross-sectional view of the elongated member. This offset distance is only about a few millimeters or a fraction of a millimeter. As shown this offset distance can very along the length of the elongated member 707.

The channels are made from a material that can stand sterilization and is robust to damage caused by a sharp instrument introduced in the guide e.g. high quality stainless steel or a suitable plastic material that can stand autoclaving or for disposable (single use) biopsy guides or assemblies a plastic material that can stand sterilization by gas or radioactive radiation. The channel 712 is held in a fixed position relative to the elongated member by means of a fixture 714.

The elongated member is made from a material that can stand autoclaving.

The channels 717 and 712 terminate at the handle-end in respective end-pieces 719 and 720 which are shaped as a convex cylinder for the operator of the probe to place two fingers and securely (single-handed) maintaining the finger grip when the instrument or needle is to be introduced into the guide. The end-pieces may optionally have a tactile surface on a portion of surface to facilitate secure handling. Preferably, marking on the end-pieces corresponds to marking of the bi-plane images acquired by means of the first transducer in side-fire mode and end-fire mode, respectively, when displayed on a display screen.

Figure 7E:
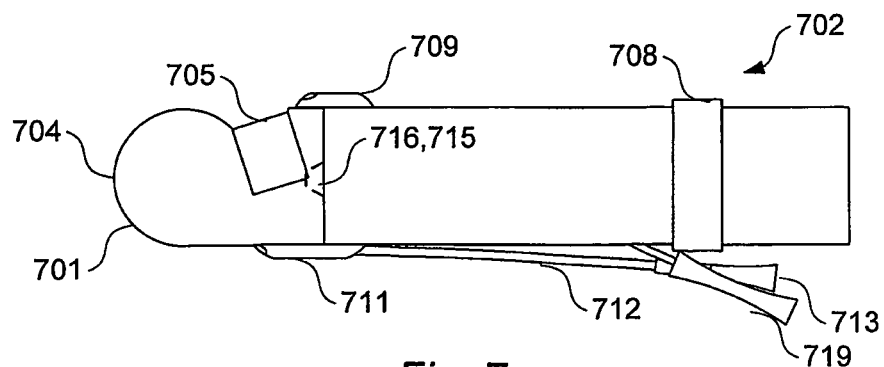
FIG. 7e shows an interconnected ultrasound probe and biopsy assembly.

FIG. 7e shows an interconnected ultrasound probe and biopsy assembly. It can be seen that the collar 708 and upper lip 709 and lower lip 711 engage with the probe. It can further be seen that the knob or pin 716 engages with the notch 715 to form a locking mechanism.

Figure 7F:
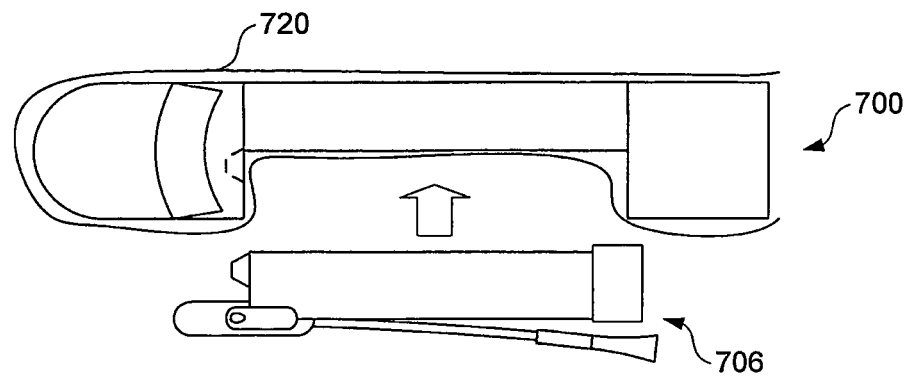
FIG. 7f shows an ultrasound probe protected by a cover.

FIG. 7f shows an ultrasound probe protected by a cover. The assembly is detached from probe, but is shown next to the probe. The probe is covered by a cover 720 such that the probe is protected from direct contact with the patient when introduced into a body cavity. Thereby disinfection of the probe after use is not needed. The probe is ready for its next use after common cleaning thereof (when the cover 720 has been removed). Thereby, the assembly 706 does not need to come into direct contact with the probe. Arranging the assembly in this manner is particularly advantageous in that a needle will not penetrate the cover 720. As a result the probe is not Unnecessarily contaminated and thus need not be disinfected after each use.

Figure 7G:
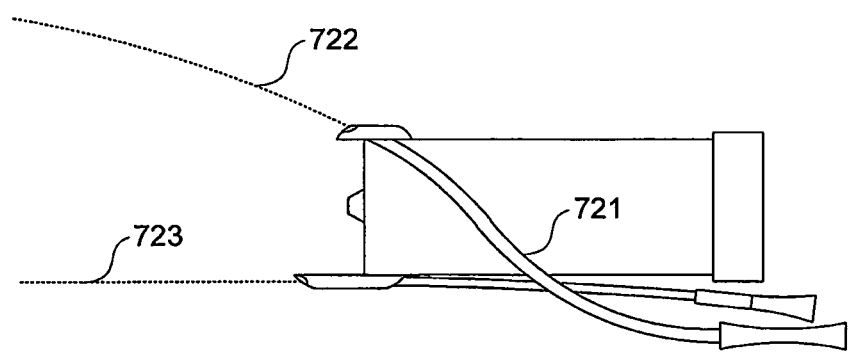
FIG. 7g shows a biopsy assembly with a curved needle guide.

FIG. 7g shows a biopsy assembly with a curved needle guide. In this embodiment the transverse guide 721 is shown as a guide with a curved channel. Thereby, the angle of protraction can be arranged with fewer constraints than a straight channel. Especially, the handle-end of the guide can be placed with fewer constraints thus allowing a more ergonomic or operator friendly design. Reference numerals 722 and 723 designate paths of the needles guided through the transverse and longitudinally extending needle guide, respectively.

Figure 8A:
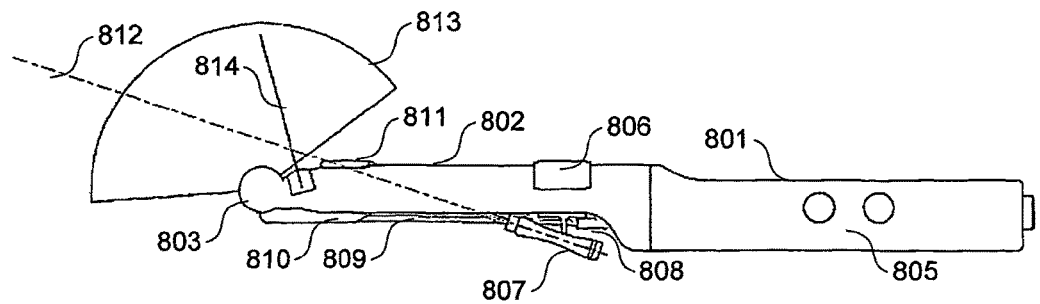
FIGS. 8a and 8b show a side-view and a 3D view of an ultrasound probe in a bi-plane mode.
Figure 8B:
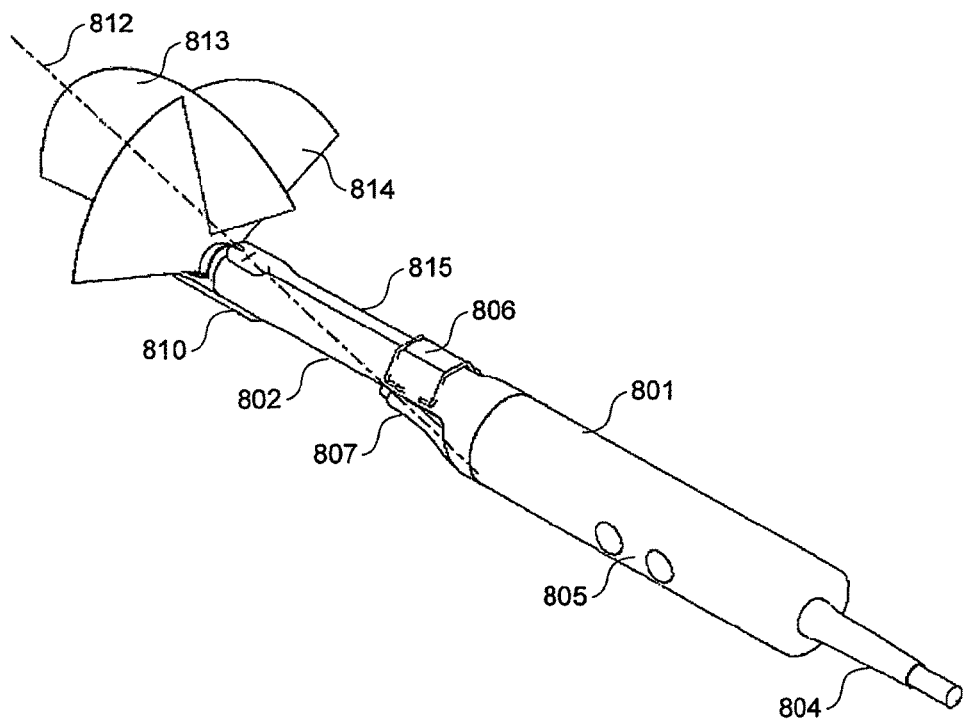

FIGS. 8a and 8b show a side-view and a 3D view of an ultrasound probe in a bi-plane mode. The probe comprises a handle 801 and a shaft 802 with a scanning head 803. The handle has two buttons 805 for shifting between modes of the probe e.g. one of the buttons selects the end-fire mode and the other selects the bi-plane mode. At the handle-end a cable connection 804 is provided.

The probe is interconnected with a biopsy assembly with an elongated member 815 which is maintained interconnected with the probe by means of a clamp 806. An upper lip 811, a lower lip 810, a longitudinal guide channel 809 and end-pieces 808 thereof is also shown. Further, an end-piece 807 of a transverse guide is also shown and the biopsy path 812 established by the transverse guide is also shown.

The probe is shown in a mode that provides bi-plane imaging with a sagittal field of view 813 and a transverse field of view 814. The sagittal field of view 813 is arranged to provide primarily a side-fire view.

Figure 9A:
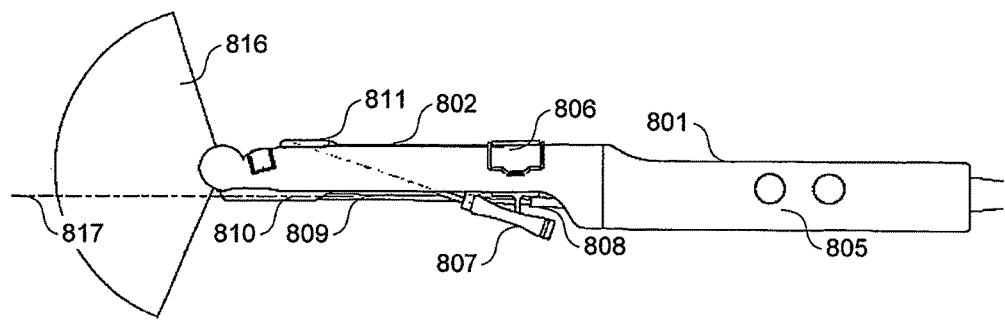
FIGS. 9a and 9b show a side-view and a 3D view of an ultrasound probe in an end-fire mode.
Figure 9B:
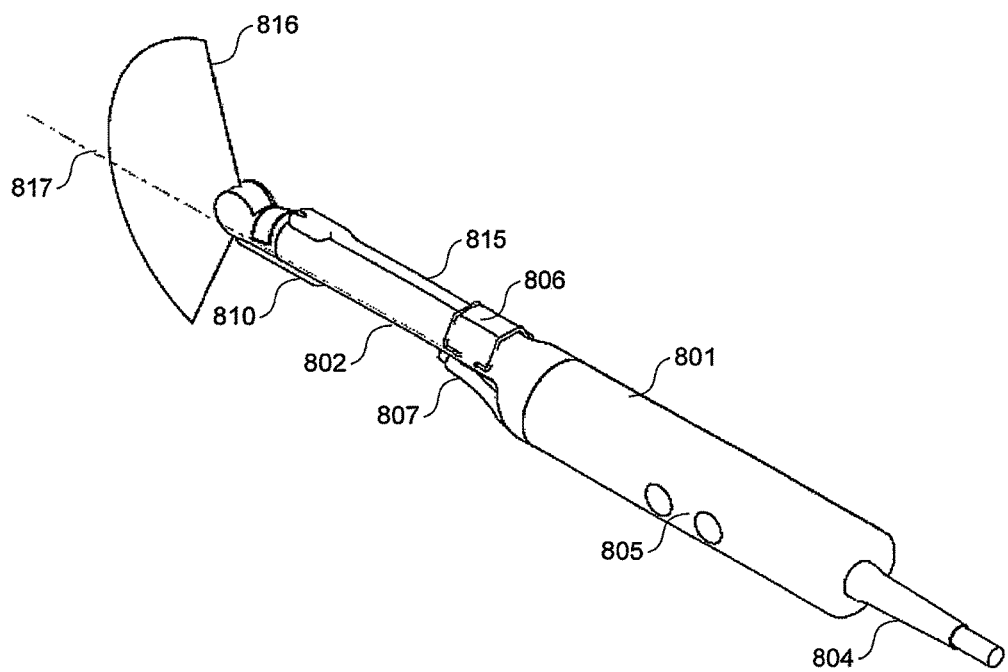

FIGS. 9a and 9b show a side-view and a 3D view of an ultrasound probe in an end-fire mode. The sagittal field of view 816 is arranged to provide primarily an end-fire view. The biopsy path 817 established by the transverse guide is also shown.

Figure 10A:
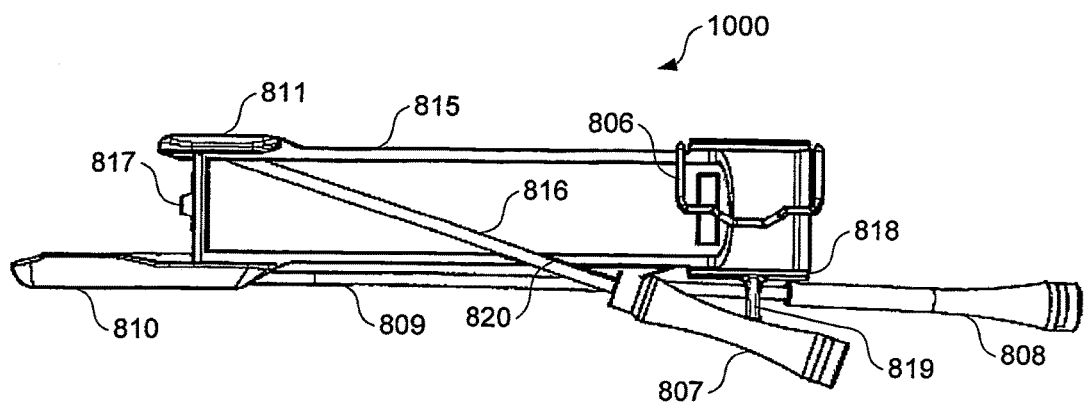
FIGS. 10a and 10b show a side-view and a 3D view of a biopsy assembly.
Figure 10B:
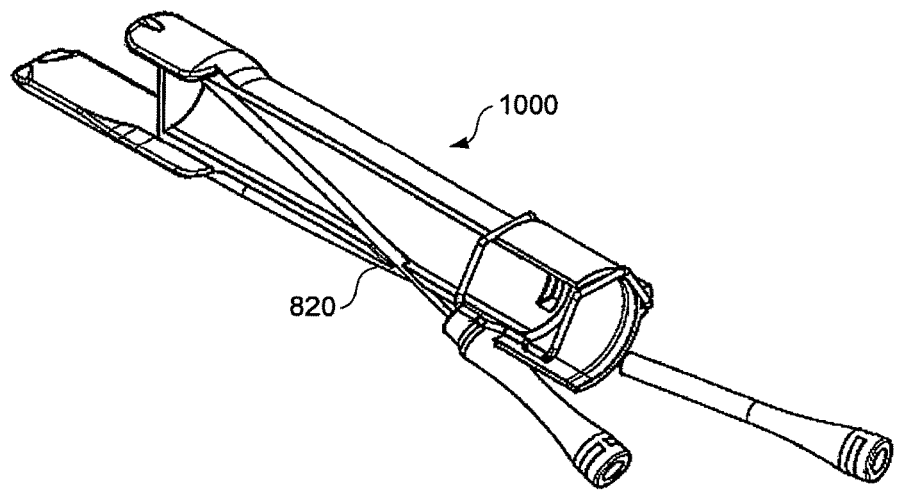

FIGS. 10a and 10b show a side-view and a 3D view of a biopsy assembly. This assembly is the biopsy assembly shown interconnected with the probe on FIGS. 8 and 9, but here shown in greater detail.

The biopsy assembly 1000 has an elongated member 815. A collar 818 provides retention or fixation of the assembly at the handle-end of the probe. At the opposite end of the elongated member a knob or pin 817 provides retention or fixation of the assembly at the distal end of the probe. Retention is further improved by an upper lip 811 and a lower lip 810 which engage with a portion of the periphery of the probe.

The upper lip 811 and lower lip 810 are configured with openings (not shown) wherefrom instruments inserted into the channels 816 and 809 can protract to follow the biopsy paths into the tissue under examination.

The needle guide 809 extends along the periphery of the elongated member 815 and is held in a fixed position in the handle-end by a fixation protrusion 819. The needle guide 816 extends transverse to the longitudinal axis of the elongated member 815 and is held in a fixed position in the handle-end by a duct 820 in the elongated member 815. The duct 820 fixates the guide by friction. At the opposite ends of the guides 816,809, the guides are fixated by the upper lip 811 and lower lip 810.

The channels 816 and 809 terminate at the handle-end in respective end-pieces 807 and 808 which are shaped as a convex cylinder for the operator of the probe to place two fingers and securely (single-handed) maintaining the finger grip when the instrument or needle is to be introduced into the guide. Preferably, marking on the end-pieces corresponds to marking of acquired bi-plane images, respectively, when displayed on a display screen. As shown the end-pieces can have a different outer shape e.g. an outer shape as concave cylinder (807) or an outer shape as a combined cylinder and cone.

It should be noted that the elongated member (101) can a rod-shaped member e.g. as shown on FIGS. 1 to 5. However, the elongated member need not accommodate an ultrasound transducer. Consequently, the depression 106 is not needed.

The invention claimed is:

1. A biopsy assembly for collecting tissue samples with a biopsy needle when introduced in a body cavity, comprising:
    an elongated member, with a longitudinal axis;
        a first needle guide structure with an axis extending in a first direction transverse to the longitudinal axis;
        a second needle guide structure that is separate from said first needle guide, wherein the second needle guide structure includes an axis extending in a second direction along the longitudinal axis of the elongated member;
        a protrusion extending from a first end of the elongated member in a direction along the longitudinal axis of the elongated member; and
        a semi-circular fixation collar disposed at a second end of the elongated member, wherein the first and second ends are opposing ends along the longitudinal axis,
    wherein the elongated member is a semi-cylindrical member with a half-circle side and a planar side and the semi-circular fixation collar is disposed at an outer perimeter of the half-circle side, wherein the first needle guide structure extends from the half-circle side through the semi-cylindrical member to the planar side and the second needle guide structure is disposed outside of a perimeter of the half-circle side.

2. The biopsy assembly according to claim 1, where the first needle guide structure is elongated and is structured to guide a needle at an angle with respect to the longitudinal axis of the elongated member within the range of 10 to 50 degrees.

3. The biopsy assembly according to claim 1 or 2, where the first needle guide structure is a tube with an entry end configured for entry of a needle and an exit end configured for at least a portion of the needle to project from the first needle guide and wherein the first needle guide structure locates the needle, when inserted into the first needle guide, at the projection of the needle from the first needle guide structure at an angle with respect to the longitudinal axis of the elongated member within the range of 10 to 50 degrees.

4. The biopsy assembly according to claim 1, where the needle guide structures are arranged, with respect to the elongated member, to make needles, when inserted into the needle guides, protract at opposite positions with respect to a cross-section of the biopsy assembly.

5. A system comprising the biopsy assembly according to claim 1 and a probe having a recess and wherein the elongated member has a shape that is configured for mechanical interconnection with the probe and to match the recess of the probe so as to provide a combination of the biopsy assembly and probe, when interconnected, that is circumscribed by a cylinder that covers at least a portion of the length of the elongated member and has a diameter that is within the range of 12 to 30 millimeters.

6. The biopsy assembly according to claim 1, where at least one of the needle guide structures is a tube with an entry end configured for entry of a needle and an exit end configured for at least a portion of the needle to project from the needle guide.

7. The biopsy assembly of claim 1, further including:
    an upper lip disposed at a first end of the half-circle side at the first end of the elongated member; and
    a lower lip disposed at a second opposing end of the half-circle side at the first end of the elongated member.

8. An ultrasound probe for cavity scanning of a body and for guiding a biopsy needle, said ultrasound probe comprising:
    an elongated body, including:
        a first end region at a first end of the elongated body;
        an ultrasound transducer providing an imaging plane, wherein the ultrasound transducer is disposed at the first end region;
        a second end region at a second end of the shaft, wherein the first and second end regions are at opposing end of the elongated body;
        an intermediate region disposed between the first end region and the second end region, wherein the intermediate region is recessed in the elongated body relative to the first and second end regions such that the elongated body includes a recess; and
        an indentation in a wall of the first end region, wherein the wall is transverse to the elongated body, and the indentation extends from the recess into the first end region; and
    a needle guide, including:
        a semi-cylindrical member with a half-circle side and a planar side;
        a first needle guide structure which guides an elongated needle in only a first direction transverse to a longitudinal axis of the probe wherein the first needle guide structure extends from the half-circle side through the semi-cylindrical member to the planar side,
        a second needle guide structure which guides an elongated needle in only a second direction longitudinal to the probe, wherein the second needle guide structure is disposed outside of a perimeter of the half-circle side; and
        a protrusion disposed on a cross-sectional side of the semi-cylindrical member, wherein the protrusion is disposed between the first needle guide structure and the second needle structure,
    wherein the indentation engages the protrusion, securing the needle guide to the elongated body.

9. The ultrasound probe of claim 8, wherein the needle guide further includes: a semi-circular collar disposed around the half-circle side of the semi-cylindrical member.

10. The ultrasound probe of claim 9, wherein the semi-circular collar includes opposing ends, wherein the opposing ends of the semi-circular collar engage the elongated body of the ultrasound probe.

11. The ultrasound probe of claim 10, wherein the needle guide includes:
    an upper lip disposed at a first end of the half-circle side; and
    a lower lip disposed at a second opposing end of the half-circle side, wherein the first and second ends of the half-circle side are across from each other with the semi-cylindrical member therebetween.

12. The ultrasound probe of claim 11, wherein the upper and lower lips engage a periphery of the elongated body of the ultrasound probe.

13. The ultrasound probe of claim 8, wherein the first needle guide structure extends through the semi-cylindrical member along a straight channel.

14. The ultrasound probe of claim 8, wherein the first needle guide structure extends through the semi-cylindrical member along a curved channel.

15. The ultrasound probe of claim 8, wherein the needle guide is removably affixed to the elongated body.

* * * * *